(12) United States Patent
Lubell et al.

(10) Patent No.: US 8,195,480 B2
(45) Date of Patent: *Jun. 5, 2012

(54) SYSTEM FOR MAINTAINING PERSON'S MEDICAL HISTORY IN PORTABLE MEMORY DEVICE

(75) Inventors: Michael Lubell, Raleigh, NC (US); Robert Guinta, Ramsey, NJ (US); Albert Moran, Jr., Hillsdale, NJ (US)

(73) Assignee: LMG 3 Marketing and Development Corporation, Hillsdale, NJ (US)

( * ) Notice: Subject to any disclaimer, the term of this patent is extended or adjusted under 35 U.S.C. 154(b) by 816 days.

This patent is subject to a terminal disclaimer.

(21) Appl. No.: 11/779,664

(22) Filed: Jul. 18, 2007

(65) Prior Publication Data

US 2008/0015905 A1    Jan. 17, 2008

Related U.S. Application Data

(63) Continuation-in-part of application No. 10/605,127, filed on Sep. 10, 2003, now abandoned.

(51) Int. Cl.
*G06Q 10/00* (2012.01)
*G06Q 50/00* (2012.01)

(52) U.S. Cl. .................................. 705/2; 705/3

(58) Field of Classification Search .................... 705/2–3
See application file for complete search history.

(56) References Cited

U.S. PATENT DOCUMENTS

| | | | |
|---|---|---|---|
| 4,868,373 A | 9/1989 | Opheij | |
| 4,996,681 A | 2/1991 | Cocco | |
| 5,461,719 A | 10/1995 | Hosoya | |
| 5,481,519 A | 1/1996 | Hosoya | |
| 5,651,067 A | 7/1997 | Ahrens | |
| 5,731,629 A | 3/1998 | Woodward | |
| 5,825,882 A | 10/1998 | Kowalski | |
| 5,832,488 A | 11/1998 | Eberhardt | |
| 5,895,455 A | 4/1999 | Bellinger | |

(Continued)

FOREIGN PATENT DOCUMENTS

CA    2545131 A1    10/2006

OTHER PUBLICATIONS

"RTS Unveils CryptoStick at Infotech, Files Patent for Portable Encryption Device," Business Wire. Oct. 30, 2002.*

*Primary Examiner* — Sheetal R Rangrej
(74) *Attorney, Agent, or Firm* — Eugene Rzucidlo; Hershkovitz & Associates, LLC

(57) ABSTRACT

A system includes a portable, hand carried nonvolatile memory device in which a person maintains his or her medical history. The portable memory device includes a program, executable by a general computer, for storing medical records in a secure database in the portable memory device, updating the medical records in the secure database, and providing access to the medical records in the secure database. The system further includes a method for recovering that person's medical history in the event of loss, destruction, or damage of the device, including the steps of: maintaining a backup copy of the secure database externally to the device, which backup copy is accessible via the Internet computer; accessing the backup copy via the Internet; copying the accessed backup copy to a replacement device, which replacement device also includes the program or an updated version of the program.

5 Claims, 5 Drawing Sheets

U.S. PATENT DOCUMENTS

| | | |
|---|---|---|
| 5,923,018 A | 7/1999 | Kameda |
| 6,021,393 A | 2/2000 | Honda |
| 6,421,650 B1 | 7/2002 | Goetz et al. |
| 6,467,690 B1 | 10/2002 | Reeves |
| 6,898,653 B2 | 5/2005 | Su et al. |
| 7,106,843 B1 | 9/2006 | Gainsboro et al. |
| 2002/0046061 A1* | 4/2002 | Wright et al. .................... 705/3 |
| 2002/0077861 A1 | 6/2002 | Hogan |
| 2002/0120470 A1 | 8/2002 | Trice |
| 2002/0128856 A1 | 9/2002 | Stefik |
| 2004/0010656 A1 | 1/2004 | Chiao |
| 2004/0078227 A1 | 4/2004 | Morris |
| 2004/0103000 A1* | 5/2004 | Owurowa et al. ................. 705/2 |

* cited by examiner

SYSTEM FOR MAINTAINING PERSON'S MEDICAL HISTORY IN PORTABLE MEMORY DEVICE

CROSS REFERENCE TO RELATED APPLICATIONS

The present application is a U.S. continuation-in-part patent application of, and claims priority under 35 U.S.C. §120 to, U.S. nonprovisional patent application Ser. No. 10/605,127, filed Sep. 10, 2003, which nonprovisional patent application is incorporated by reference herein.

BACKGROUND OF THE INVENTION

This invention relates to a secure portable device for storing and accessing patient records.

Accurate, accessible and shareable health information is a well accepted prerequisite of good healthcare. Patient safety, public safety, continuity of patient care, healthcare economics, clinical research and outcomes analysis are adversely affected by the reduced quality of health information available. The prior art has attempted to solve these problems in the healthcare field in not entirely satisfactory ways. The following patents are illustrative of the prior art attempts at medical record storage.

U.S. Pat. No. 5,832,488 to Eberhardt discloses a computer system and method for programming data of an individual's medical histories on a storage device. The programs are designed to record information on smart cards such as patient identifier and a running medical history plus pharmaceutical information. U.S. Pat. No. 6,467,690 to Reeves discloses an electronic storage memory card of a particular type which is capable of having digital binary data stored within its surface and which is easily carried on a person in a wallet or purse.

U.S. Pat. No. 5,731,629 to Woodward discloses a personal data storage device for storing information such as medical records and a system for storing and reading such information from the storage device.

Also of some interest are U.S. Pat. Nos. 5,932,759 and 5,825,882 and patent publications 2002/0128856 and 2002/0120470.

Recently, an attempt was made to embed a 32 k chip beneath a person's skin with patient information that was uploaded to the chip. The significant disadvantage to this format was that it required surgery with a cost factor and the information on the chip was limited. Furthermore, since the filing of the parent patent application (Ser. No. 10/605,127) of this patent application, additional solutions have been proposed such as those presented in published Canadian Patent Application Serial No. 2,545,131, which patent reference is incorporated herein by reference.

The unique device of this invention is not disclosed or suggested in the prior art and provides a novel solution to medical record problems.

SUMMARY OF THE INVENTION

This invention comprises a portable, secure, self-contained memory device that in combination with MyRECS™ copyrighted software is designed to store, update and display personal medical information. The MyRECS™ device is a small hand carried device which is connectible to the USB port of a computer or reader adapter. Access to the medical information is provided by a unique password. Medical information stored in the device cannot be deleted or changed—it can only be appended.

The MyRECS™ device stores personal information, emergency contact information along with reports, referral letters, images, medications, immunizations, medical conditions, allergies, surgeries, medical alerts, and any other pertinent information required to treat a person correctly. Each device is registered to a particular individual and the information is kept in a secure encrypted database. In an emergency, if the user is incapacitated, an 800 phone number may be used to unlock the device and view the information.

Accordingly an object of this invention is to provide a new and improved small, portable memory device for storing medical records.

Another object of this invention is to provide a new and improved portable, secure, self-contained memory device that functions with software to store, update and display personal medical information.

A further object of this invention is to provide a new and improved portable storage device for medical records which is accessed by a unique password but may be unlocked in emergencies through a customer service center.

A more specific object of this invention is to provide a new and improved small portable memory device to store, update, and accurately display personal medical information using a password which information cannot be deleted, only appended and which may be inputted by scanning, keying or downloading.

BRIEF DESCRIPTION OF DRAWINGS

The above and other objects of this invention may be more clearly seen when viewed in conjunction with the accompanying drawings.

DETAILED DESCRIPTION

Figure 3:
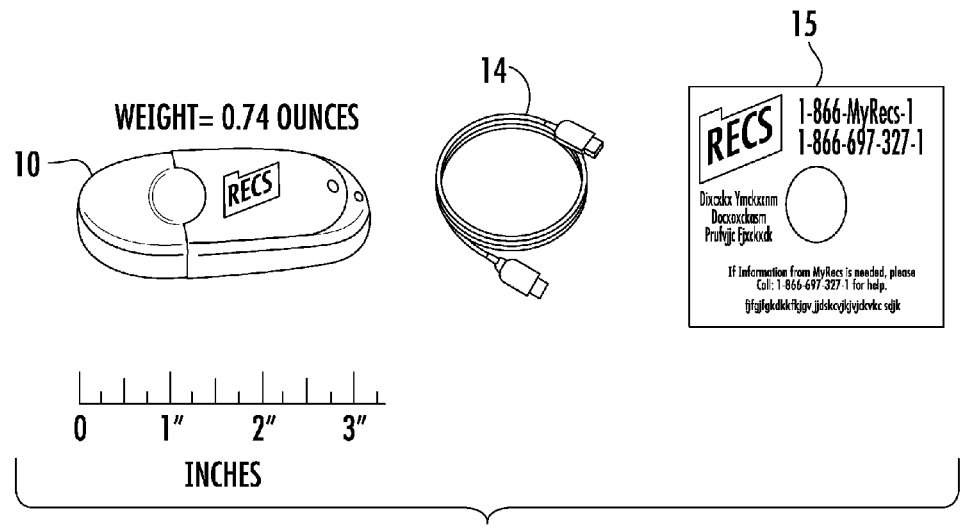
FIG. 3 illustrates a small portable memory device, USB extender cable, and CD-ROM in accordance with an implementation of an embodiment of the invention.
Figure 4A:
FIGS. 4a, 4b and 4c each respectively illustrate a screenshot in accordance with an implementation of an embodiment of the invention.
Figure 4B:
Figure 4C:
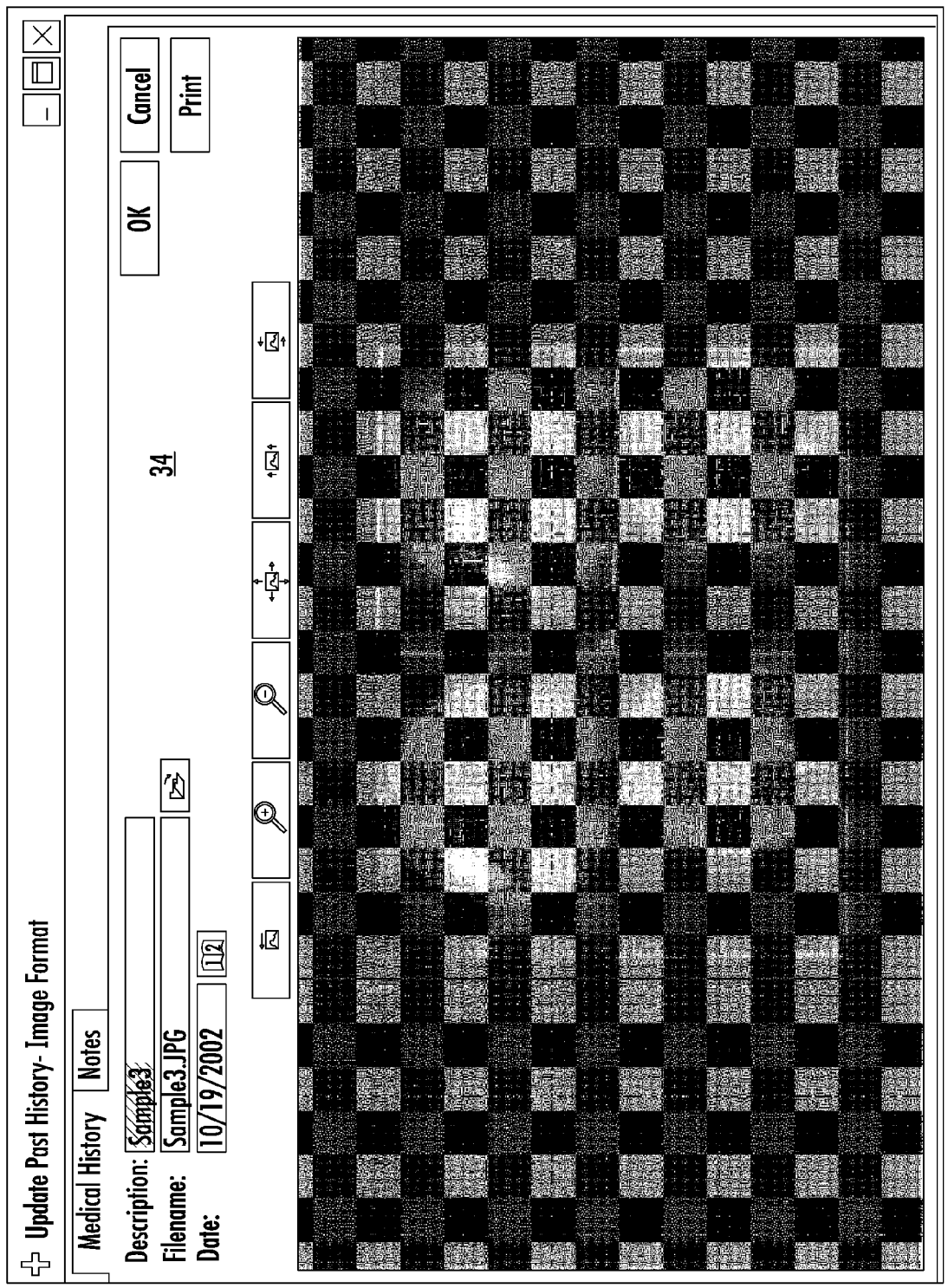

In accordance with an implementation of a commercial embodiment of the invention, and as illustrated in FIG. 3, a small, portable, hand carried device 10 is provided that is marketed under the brand MyRECS™ by LMG Marketing and Development Corporation of Ramsey, N.J. The device 10 includes a USB connector at one end and a removable cap that covers the USB connector when the device 10 is not in use.

As further shown in FIG. 3, a USB extender cable 14 and a business card size CD-ROM 15 are also provided. The CD-ROM contains WIN 98 drivers for computer systems with operating systems that are not WINDOW 2000 or XP. The device 10 includes software 11 that is designed to store, compile, update and display a person's medical history. The information is kept in a secure encrypted database. In alternative embodiments, the small, portable, hand carried device can be any nonvolatile memory device such as a USB drive, memory stick, digital card and flash memory card that is read through a standard memory card reader. HIPAA compliant software may also be included.

The MyRECS™ device 10 is plugged into the USB port 16 of any PC based computer 17 and the medical history of the owner is immediately available and viewable. From the patient's perspective, the device 10 is totally portable and can hold up to 48,000 pages or 120 images, or any combination thereof. The capacity of the memory device is only limited by the size of the USB drive. For example, it is believed that 64 MB of memory provides storage for 96,000 pages and 240 images, and 128 MB of memory provides storage for 192,000 pages and 440 images. This eliminates bulky files and folders.

From the doctor's perspective, the MyRECS™ device 10 will allow any doctor, anywhere, to have all a patient's pertinent medical history available immediately with the patent's permission. This device 10 provides information such as name, address, phone, emergency contact, primary physician contact, medical alerts, allergies, medical conditions, medications (active/inactive), immunizations, blood type, surgeries, medical history, treatments, etc.

Significant advantages to having such patient information readily available to the medical community and insurance companies may include:

A) Increases in proper initial diagnosis of patients.
B) Reductions in ordering of expensive medical tests.
C) The prescribing of medications and dosages which are more precise and specific to the patient's medical condition.
D) Reductions in unnecessary admissions to hospitals.
E) Reductions in patient deaths and complications due to medical errors.

In summary, the MyRECS™ device 10 is a small, portable, hand carried, secure, self-contained memory device that, in combination with software stored therein, is designed to store, compile, update and display a person's medical history. Healthcare providers may access this stored medical information only when given a unique password by the patient. Medical information stored in the device 10 cannot be deleted or changed. It can only be appended. Reports show added information, which are date and time stamped, and also show the name of the party adding the information. It is believed that the device meets all legal privacy requirements.

The combination of software and hardware makes this device unique. The device 10 is self-contained with the only exception of a computer with a USB port needed to view the information stored in the database on the device 10. No website or external database is required to store and retrieve information. Information can be put on the device 10 by direct input from a keyboard into the MyRECS™ software program 11. Information can also be scanned directly to the device 10 and input from a computer on the device 10.

Information can be imported from over twenty-five file types from various file formats and saved on the device 10 which can then be read by software 11 and viewed. The device 10 thus and has the capability to integrate with various and numerous medical software applications. Information can be transferred from a file on a computer to the device 10 and read. Further, information stored on the device 10 can also be copied to a patient's medical record at a physician's office or hospital reducing the chance of human error in recreating the information. The information can be created in any word processing program or spreadsheets such as Microsoft Office or Word Perfect or any text based or graphic application and copied and pasted to the software 11 or saved as a file and copied to the device 10 or from EMR software.

The patient's medical record may also be stored in a secured secondary site that will also permit a patient to reload their information in the event their device 10 is lost, destroyed, damaged or a larger memory device 10 is required. The backup would be provided by a Data Recovery Center (DRC).

Figure 1:
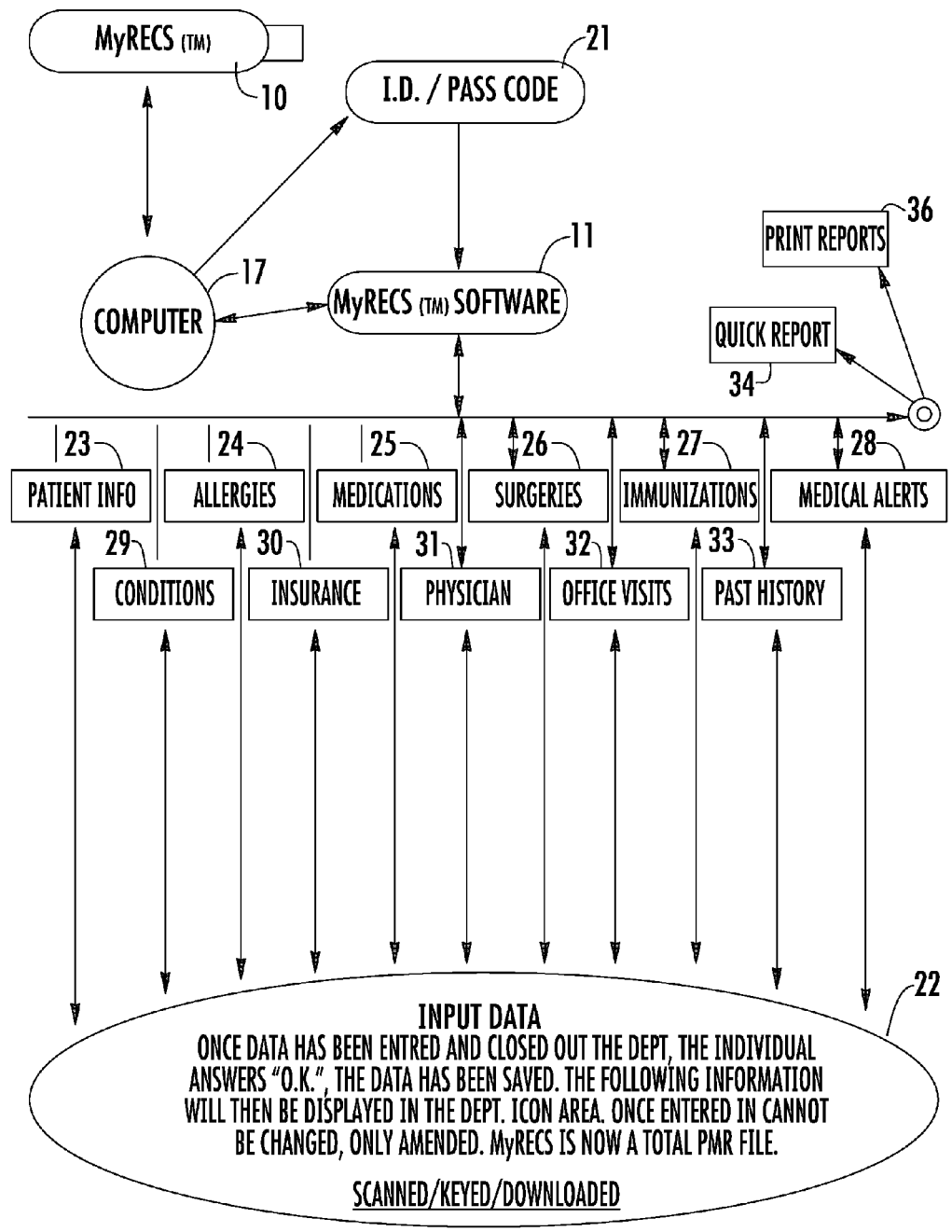
FIG. 1 is a schematic illustration showing aspects and features of an embodiment of the invention.

As represented in FIG. 1, the MyRECS™ device 10 is disposed in electronic communication with computer 17 via a USB port of the computer 17. A patient I.D. or pass code 21 is supplied to the software 11. Input data 22 may be scanned, keyed or downloaded into the MyRECS™ software 11. Patient information 23, allergies 24, medications 25, surgeries 26, immunizations 27, medical alerts 28, conditions 29, insurance 30, physicians 31, office visits 32, and past history 33 are typical entries to the computer 17 and associated software 11. If desired, a quick report 34 or complete report 36 may be printed or viewed on the screen of computer 17.

Figure 2:
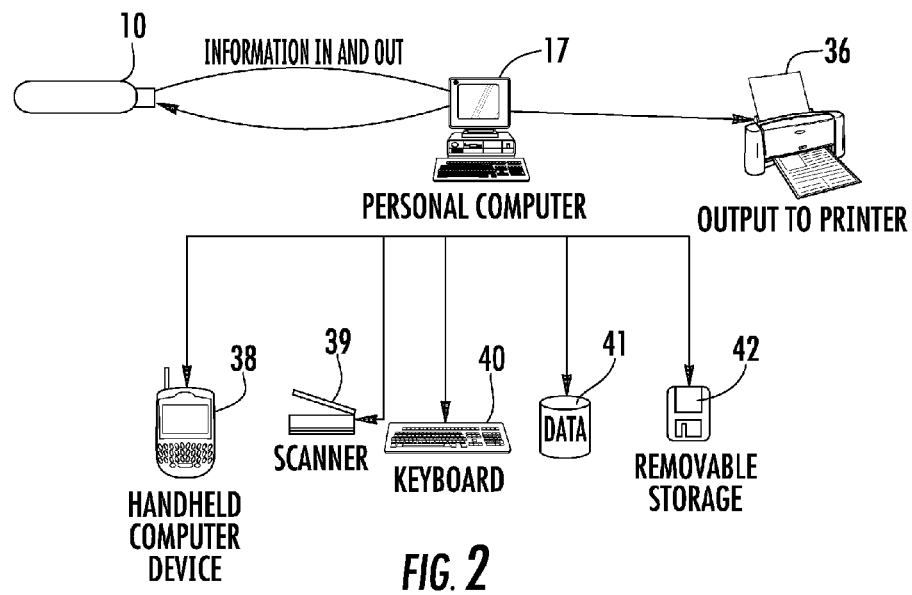
FIG. 2 illustrates an environment in which an implementation of an embodiment of the invention is used.

FIG. 2 illustrates an environment in which the device 10 may be used. The MyRECS™ device 10 both provides and receives information from the computer 17. The computer 17 may also feed information to the printer 36. Coupled to the computer 17 are a handheld computer 38, a scanner 39, a keyboard 40, data 41 and removable storage 42.

While the invention has been explained by a detailed description of certain specific embodiments, it is understood that various modifications and substitutions can be made in any of them within the scope of the appended claims, which are intended also to include equivalents of such embodiments.

What is claimed is:

1. In a system in which a person maintains his or her medical history in a portable, hand carried nonvolatile memory device comprising machine-readable memory having software comprising machine-executable instructions constituting a program executable by a general computer for (i) storing medical records in a secure database in the machine-readable memory of the portable, hand carried memory device, (ii) updating the medical records in the secure database in the machine-readable memory of the portable, hand carried memory device, and (iii) providing access to the medical records in the secure database in the machine-readable memory of the portable, hand carried memory device, a method for recovering that person's medical history in the event of loss, destruction, or damage of the device, the method comprising the steps of:

(a) maintaining a backup copy of the secure database externally to the hand carried device, which backup copy is accessible via an Internet computer;

(b) accessing the backup copy via the Internet;

(c) copying the accessed backup copy to a replacement hand carried device, which replacement hand carried device includes software which comprises a program executable by a general computer for (i) storing medical records in a secure database in the machine-readable memory of the portable, hand carried memory device, (ii) updating the medical records in the secure database in the machine-readable memory of the portable, hand carried memory device, and (iii) providing access to the medical records in the secure database in the machine-readable memory of the portable, hand carried memory device;

(d) wherein said steps (h) and (c) are performed using a general computer.

2. The system of claim 1, wherein the person whose medical history is recorded, updated, and accessed-carries the replacement hand carried device on his or her person.

3. The system of claim 1, wherein the secure database and the backup copy of the secure database is encrypted.

4. The method of claim 1, wherein each of the secure database and the backup copy of the secure database includes information pertinent to the treatment of the person, comprising:
   (a) personal information including name, address, phone, and emergency contact information;
   (b) emergency medical information including medical alerts, blood type, allergies
   (c) current medical information including primary physician contact, medical conditions, medications, and treatments;
   (d) historical medical information including a log of medical office visits, physicians, images from medical scans, a log of vital statistics, immunizations, and surgeries; and
   (e) insurance information including referral letters.

5. The method of claim 1, wherein the hand carried device comprises a USB memory device, a flash memory device, or a memory stick; and wherein the replacement hand carried device comprises a USB memory device, a flash memory device, or a memory stick.

* * * * *